United States Patent
Lin et al.

(10) Patent No.: US 7,898,666 B2
(45) Date of Patent: Mar. 1, 2011

(54) METHOD AND APPARATUS FOR ROBUST DETECTION OF THE DENSITY OF A PIGMENTED LAYER

(75) Inventors: Julianna Elizabeth Lin, Rochester, NY (US); Aaron Michael Burry, Ontario, NY (US); Peter Paul, Webster, NY (US); William C. Dean, Webster, NY (US); William Lee Kennedy, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 637 days.

(21) Appl. No.: 11/833,633

(22) Filed: Aug. 3, 2007

(65) Prior Publication Data

US 2009/0033918 A1    Feb. 5, 2009

(51) Int. Cl.
*G01N 21/55* (2006.01)

(52) U.S. Cl. .......................... 356/445; 356/402

(58) Field of Classification Search .................. 356/445, 356/402
See application file for complete search history.

(56) References Cited

U.S. PATENT DOCUMENTS

| | | | | |
|---|---|---|---|---|
| 4,561,016 A | * | 12/1985 | Jung et al. ................ | 358/527 |
| 4,980,723 A | * | 12/1990 | Buddendeck et al. ......... | 399/72 |
| 4,999,673 A | * | 3/1991 | Bares ...................... | 399/49 |
| 5,140,342 A | * | 8/1992 | Metildi et al. ............. | 347/232 |
| 5,170,257 A | * | 12/1992 | Burns ...................... | 358/3.21 |
| 5,337,122 A | * | 8/1994 | Hubble et al. .............. | 399/49 |
| 5,387,977 A | * | 2/1995 | Berg et al. ................ | 356/407 |
| 5,477,317 A | * | 12/1995 | Edmunds et al. ............. | 399/39 |
| 5,691,817 A | * | 11/1997 | Cargill et al. ............. | 356/405 |
| 5,953,104 A | * | 9/1999 | Matsumoto .................. | 355/40 |
| 6,760,121 B1 | * | 7/2004 | Kimura et al. .............. | 358/1.7 |
| 7,054,568 B2 | | 5/2006 | Mizes et al. | |
| 2003/0048449 A1 | * | 3/2003 | Vander Jagt et al. ......... | 356/432 |
| 2004/0033427 A1 | * | 2/2004 | Coveleskie et al. .......... | 430/30 |
| 2004/0048175 A1 | * | 3/2004 | Bobeck et al. .............. | 430/30 |
| 2004/0063010 A1 | * | 4/2004 | Coveleskie et al. .......... | 430/30 |
| 2005/0214015 A1 | * | 9/2005 | Friedrich .................. | 399/74 |

* cited by examiner

*Primary Examiner* — Roy Punnoose
(74) *Attorney, Agent, or Firm* — Oliff & Berridge, PLC

(57) ABSTRACT

Aspects of the disclosure can provide a method of detecting a density of a pigmented layer on an object. The method can include emitting a first modulated light onto a first portion of the object having the pigmented layer, detecting a first reflected light of the first modulated light from the first portion of the object, and determining the density of the pigmented layer according to the first reflected light. Furthermore, the method can include emitting a second modulated light onto a second portion of the object, detecting a second reflected light of the second modulated light from the second portion of the object, and determining the density of the pigmented layer according to a relative ratio that is related to the first reflected light and the second reflected light.

34 Claims, 3 Drawing Sheets

METHOD AND APPARATUS FOR ROBUST DETECTION OF THE DENSITY OF A PIGMENTED LAYER

BACKGROUND

Generally, a concern of printing industry is printing quality control. For example, U.S. Pat. No. 7,054,568 entitled "Method and Apparatus for Controlling Non-Uniform Banding and Residual Toner Density Using Feedback Control" has addressed various quality problems. For example, in a xerographic printing system, printing quality can be affected by incomplete transfer of a toner image from a photoreceptor to an intermediate transfer belt or from the intermediate transfer belt to a paper. Because of some strongly adhering toner particles, low charge toner particles, air breakdown, or other reasons, the transfer of the image from the photoreceptor to the intermediate transfer belt or the paper, or from the intermediate transfer belt to the paper, can be incomplete. If toner transfer efficiency varies significantly, toner density on a final image may change. If the final image is a colored image, then changes in the toner density can result in color shift.

U.S. Pat. No. 7,054,568 proposes a technique using a feedback control system to address various quality control problems that may happen in a printing system. Generally, a feedback control system can include a working system, a monitoring system, and a controlling system. The monitoring system can monitor the working system, measure parameters of the working system and provide to the controlling system. The controlling system can analyze variations of the working system based on the parameters provided by the monitoring system. Accordingly, the controlling system can send instructions to adjust the working system. In order for the feedback control system to work well, the monitoring system needs to accurately measure parameters of the working system in real-time. However, due to limitations of the monitoring system, the environment noise, defects in the working system or other disturbance, it can be difficult for the monitoring system to measure accurately.

SUMMARY

The present disclosure can provide a method and apparatus that can be utilized in a monitoring system, such as the monitoring system in a printing system, to quickly and accurately acquire information related to the printer's operation, subsequently the printing system can be adjusted according to the information.

Aspects of the disclosure can provide a method of detecting a density of a pigmented layer on an object. The method can include emitting a first modulated light onto a first portion of the object having the pigmented layer, detecting a first reflected light of the first modulated light from the first portion of the object, and determining the density of the pigmented layer according to the first reflected light.

To determine the density of the pigmented layer according to the first reflected light, one embodiment includes keeping a constant status of the first modulated light, pre-calibrating a density relationship with the reflected light based on the constant status of the first modulated light, and determining the density of the pigmented layer according to the density relationship with the reflected light and the first reflected light.

To keep the constant status of the first modulated light, one aspect of the disclosure includes calibrating the constant status according to a known density. Alternatively, another aspect of the disclosure includes monitoring the status of the first modulated light, and controlling the status of the first modulated light according to a feedback of the monitored status of the first modulated light.

To determine the density of the pigmented layer according to the first reflected light, one embodiment includes calculating a ratio of an amplitude of the first reflected light by an amplitude of the first modulated light, and determining the density of the pigmented layer according to the ratio.

According to one embodiment, the amplitude of the first modulated light is measured through a beam splitter and a detector.

According to another embodiment, the amplitude of the first modulated light is an amplitude of a first driving current.

According to the disclosure, to determine the density of the pigmented layer according to the first reflected light, one embodiment includes emitting a second modulated light onto a second portion of the object, detecting a second reflected light of the second modulated light from the second portion of the object, and determining the density of the pigmented layer according to a relative ratio that is related to the first reflected light and the second reflected light.

To determine the density of the pigmented layer according to the relative ratio that is related to the first reflected light and the second reflected light, one embodiment further includes calculating the relative ratio by dividing an amplitude of the first reflected light by an amplitude of the second reflected light.

According to one embodiment, to determine the density of the pigmented layer according to the relative ratio that is related to the first reflected light and the second reflected light, the method can include calculating a first ratio by dividing an amplitude of the first reflected light by an amplitude of the first modulated light, calculating a second ratio by dividing an amplitude of the second reflected light by an amplitude of the second modulated light, and calculating the relative ratio by dividing the first ratio by the second ratio.

According to the disclosure, the light can be modulated by sinusoidal, triangular, step or other patterns.

Aspects of disclosure can also direct to a method that uses at least one of analog filtering, signal processing techniques including Fourier analysis, and digital filtering to extract the amplitude of the modulated signals.

Aspects of the disclosure can also provide a sensor system that detects a density of a pigmented layer of an object. The sensor system can include an emitter that emits a modulated light onto a portion of the object, a detector that detects a reflected light from the portion of the object, and a controller that is coupled to the emitter and the detector, the controller determines the density of the pigmented layer of the object based on the detected reflected light.

In addition, the disclosure can direct to a printing system that can include an object that is at least one of a photoreceptor drum, a photoreceptor belt, an intermediate transfer belt, an intermediate transfer drum and paper, the object has a pigmented layer, a sensor system that detects a density of the pigmented layer of the object. The sensor system can include an emitter that emits a modulated light onto a portion of the object, a detector that detects a reflected light from the portion of the object, and a controller that is coupled to the emitter and the detector, the controller determines the density of the pigmented layer of the object based on the reflected light. The controller can adjust the printing system according to the detected density of the pigmented layer.

BRIEF DESCRIPTION OF THE DRAWINGS

Various exemplary embodiments of this disclosure will be described in detail with reference to the following figures, wherein like numerals reference like elements and wherein.

EMBODIMENTS

In a printing system, it can be important to maintain the quality of print outcome independent of any variations in the environment or materials. One approach can be using a feedback control system. The feedback control system can include a working system, a monitoring system and a controlling system. The controlling system can adjust the working system based on various parameters measured by the monitoring system. To successfully implement the feedback control system, accurate and real-time monitoring needs to be achieved.

Figure 1:
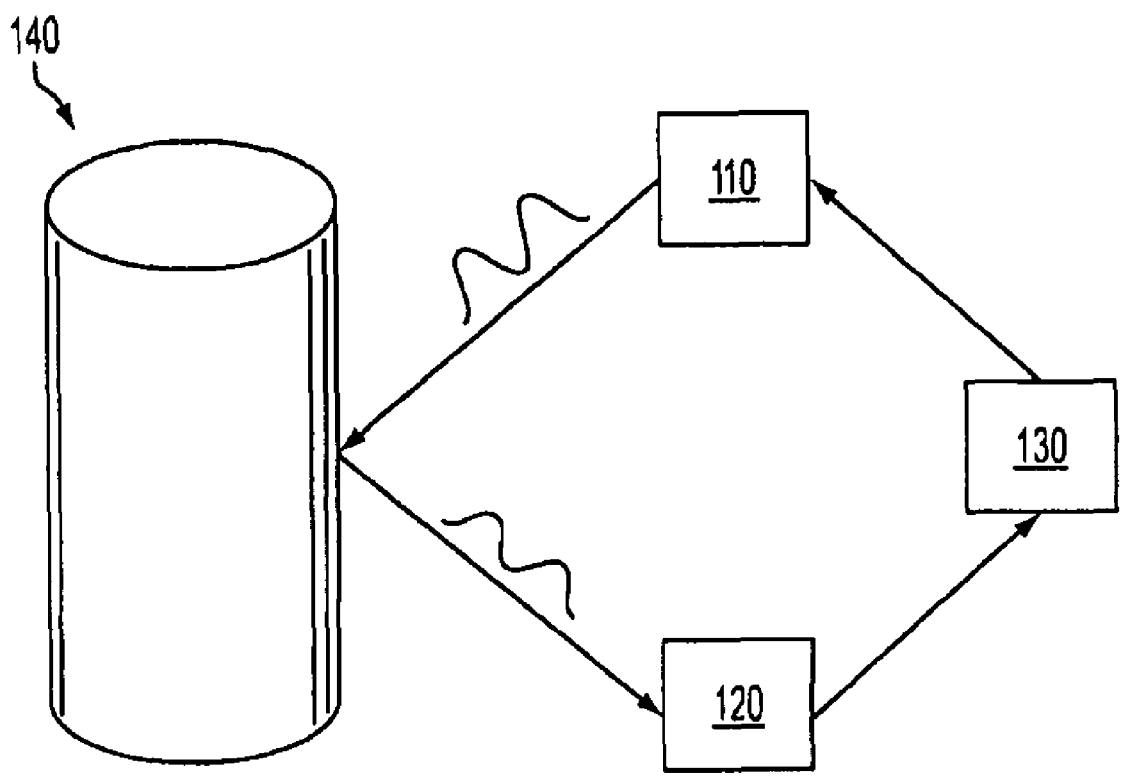
FIG. 1 is a diagram of an exemplary sensor system.

FIG. 1 is an exemplary sensor system 100 that can be used in the monitoring system to measure a parameter of an object 140. Generally, the sensor system 100 can include an emitter 110, a detector 120, and a controller 130 that can be coupled with the emitter 110 and the detector 120.

The emitter 110 can emit a signal with controlled properties. The detector 120 can then detect the signal after it is affected by the object 140. The controller 130 can define and analyze the properties of the emitted and detected signals, and determine the parameter of the object 140.

Various sensor systems can be used in a printing system to monitor various parameters of the printing system. Among them, optical densitometers, such as the Enhanced Toner Area Coverage Sensor (ETACS) and Automatic Density Control (ADC) sensor can be utilized to measure a parameter, such as relative reflectance or optical density, that is related to a density (mass density) of a toner layer on a surface, such as a density of a toner layer on a photoreceptor.

Using an optical densitometer as an example, the emitter 110 can include one or more LED(s). The LED(s) can emit light in accordance to an electrical driving current. The driving current can be controlled by the controller 130. For example, the controller 130 can change a magnitude of the driving current. In accordance, the emitter 110 can emit light with different intensity. Furthermore, the controller 130 can change the magnitude according to a specific pattern, such as sinusoidal pattern, step pattern or triangular pattern. Additionally, the controller 130 can change the magnitude of the driving current periodically with a specific frequency.

The emitted light can be directed to a portion of the object 140. According to a circumstance of a material on the portion of the object 140, the light can be affected and reflected. The reflected light can be detected by the detector 120. The detector 120 can then generate a signal in proportion to the intensity of the light detected, such as a voltage signal with an amplitude proportional to the intensity of the light detected.

As already known, some types of toner particles can absorb light, thus reduce the intensity of the reflected light, other types of toner particles can scatter light, which can increase the intensity of the reflected light. The change of the intensity of the reflected light to the emitted light can be related to toner density. Therefore, higher toner density can make larger change of light intensity. As the type of toner is pre-known, a change of light intensity between the emitted light and the reflected light can be related to the density of toner on the portion of the object 140.

Generally, a reflectance characteristic can be used to describe the relationship of the reflected light with the emitted light. Practically, the optical densitometer can use an amplitude of the emitter driving current as a measure for the intensity of the emitted light, and use an amplitude of the detector output voltage as a measure for the intensity of the reflected light. Therefore, the reflectance characteristic can be represented as a response characteristic of detector output voltage to emitter driving current.

Figure 2:
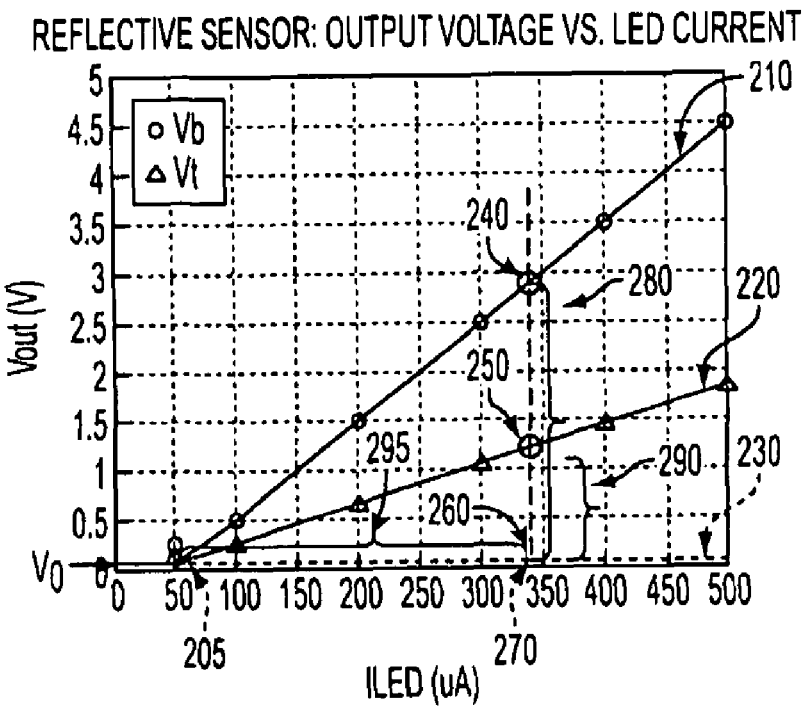
FIG. 2 is a diagram illustrating a constant intensity method for detecting toner density based on a reflectance characteristic of an object.

FIG. 2 is a diagram showing exemplary response characteristics of an object 140. Response characteristics of the object 140 for two different circumstances have been illustrated. In one circumstance, a portion of the object 140 has a layer of a specific toner, the reflectance characteristic can be represented by response characteristic line 220. In another circumstance, a portion of the object 140 can be without any layer of toner, the reflectance characteristic can be represented by response characteristic line 210. Furthermore, line 230 can be used to indicate a baseline voltage. The baseline voltage 230 is the output voltage of the detector 120 when the emitter 110 is turned off.

The response characteristic lines 210 and 220 can have a similar trend that when the emitter driving current is larger, the detector 120 can generate larger voltage. This can mean that when the emitter 110 emits light of higher intensity, the detector 120 can detect light of higher intensity. Moreover, when the emitter driving current is the same for the two response characteristic lines, less output voltage can be expected from the response characteristic line 220, which represents the reflectance characteristic of the portion of object 140 having a layer of the specific toner. The reason can be that the specific toner can absorb light, then less light can be reflected. Accordingly, less light can be detected by the detector 120. Consequently, the output voltage of the detector 120, which is proportional to the light detected, can be smaller.

The optical densitometer can use the amplitude of output voltage generated by the detector 120 to evaluate the toner density on the surface of the object 140. For example, when the emitted light is constant, a toner density relationship with output voltage can be pre-calibrated. In accordance to the toner density relationship with output voltage, the amplitude of the output voltage can be directly related to the toner density.

Moreover, the optical densitometer can detect a relative reflectance, which can be used to more accurately estimate the toner density on the surface of the object 140. To detect the relative reflectance, light emitted from the emitter 120 can be directed to a first portion of the object 140 having a layer of toner. Additionally, the light emitted from the emitter 120 can also be directed to a second portion of the object 140. Generally, the second portion of the object can be bare surface, which can be considered as free of any toner layer. In one embodiment, the first and second portions of the object 140 can be two different locations on the object 140. Alternatively, the first and second portions of the object 140 can be the same location. This can be implemented by a clean-up that can be performed before directing light onto the second portion of the object 140.

Subsequently, the relative reflectance can be calculated by dividing a first ratio by a second ratio. The first ratio can be calculated by dividing an amplitude of the reflected light by an amplitude of the emitted light associated with the first portion of the object 140. Similarly, the second ratio can be calculated by dividing an amplitude of the reflected light by an amplitude of the emitted light associated with the second portion of the object 140. The relative reflectance can be used to estimate the toner density on the first portion of the object 140.

FIG. 2 can be used to illustrate a method of detecting the relative reflectance. The method can be called constant intensity method because the method uses a constant emitter driving current. As shown in FIG. 2, the controller 130 can instruct a constant current driving the LED(s) of the emitter 110, such as a driving current 270, approximately 340 µA. The LED(s) can emit light when the driving current is larger than a turn-on current 205, which is approximately 50 µA. Accordingly, an effective current 295 can be determined by calculating the difference between the driving current 270 and the turn-on current 205. The effective current 295 is approximately 290 µA.

When the emitter 110 directs light onto the first portion of the object 140 that is with a layer of the specific toner, according to the response characteristic line 220, the detector 120 can generate an output voltage 250, approximately 1.2V. The difference of the output voltage 250 to the baseline voltage 230 is indicated by a voltage difference 290, which is approximately 1.1V. The voltage difference 290 can be considered as a voltage output due to the reflected light from the first portion of the object 140.

When the emitter 110 directs light onto the second portion of the object 140 that is without toner, according to the response characteristic line 210, the detector 120 can generate an output voltage 240, approximately 2.8V. The difference of the output voltage 240 to the baseline voltage 230 is indicated by a voltage difference 280, which is approximately 2.7V. The voltage difference 280 can be a voltage output due to the reflected light from the second portion of the object 140.

According to one technique, the voltage difference 290 can be used to evaluate the density of the specific toner. A voltage-density relationship can be pre-calibrated for various densities using a constant emitter driving current. In accordance to the voltage-density relationship, a density corresponding to the voltage difference 290 can be determined.

According to another technique, a relative reflectance (RR) can be determined. The relative reflectance can be defined as dividing a first ratio by a second ratio. The first ratio is a ratio of the voltage difference 280 to the effective driving current 295. The second ratio is a ratio of the voltage difference 290 to the effective driving current 295. The relative reflectance can be represented by equation 1:

$$RR = \frac{(V_t - V_0)/(I_d - I_0)}{(V_b - V_0)/(I_d - I_0)} = \frac{V_t - V_0}{V_b - V_0} \quad (1)$$

where $V_t$ is the output voltage of the detector 120 when the emitted light is directed to the first portion of the object 140, $V_0$ is the baseline voltage, and $V_b$ is the output voltage of the detector 120 when the emitted light is directed to the second portion of the object 140. $I_d$ is the constant emitter driving current, and $I_0$ is the turn-on current. As can be seen, equation 1 can be simplified by canceling the common terms of the emitter driving current.

In reality, the detection of toner density may be affected by various noises, such as drift noise, random noise, and periodic noise. Drift noise can be the noise that has consistent value. Random noise can be the noise that randomly changes value. Periodic noise can be the noise that periodically changes value.

Due to the presence of noises, the constant intensity method can be inaccurate when toner density is low. For example, in order to evaluate the toner transfer efficiency, it is necessary to monitor a toner density on the photoreceptor surface after the transfer of toner image to the intermediate transfer belt or the paper. In such a case, the density of the remaining toner particles on the photoreceptor surface can be very low. Accordingly, the remaining toner particles can make very small change to the reflected light. Under such a circumstance, the intensity of the reflected light from the first portion of the object 140 can be close to the intensity of the reflected light from the second portion of the object 140. Using FIG. 2 as an example, the first portion of the object can be the photoreceptor surface after the transfer of image of the specific toner. Then the output voltage of the detector 120 corresponding to the first portion of the object 140 should be close but smaller than the output voltage corresponding to the second portion of the object 140, which is toner free. However, in reality, the output voltage corresponding to the first portion may be larger than the output voltage corresponding to the second portion. This is due to the noises. Thus, the constant intensity method may not accurately evaluate the toner density when the toner density on the photoreceptor surface is low.

In order to utilize the optical densitometer to monitor low toner coverage, one method uses customized test pattern, which can be a series of evenly spaced patches. Then signal processing techniques can be used to extract the signal components of specific frequencies. Therefore, the noise components that can have different frequencies from the specific frequencies can be excluded. However, the result from this method can be pattern dependant. In addition, using patches of sharp edges can increase signal components of higher harmonic frequencies. Thus, in order to improve the accuracy of density detection, signal components of higher harmonic frequencies need to be calculated. Consequently, the calculation of toner density can be complicated.

The disclosure proposes using an emitted light of modulated intensity instead of constant intensity to detect the toner density. In particular, the intensity of the light can be modulated sinusoidally with a desired frequency to improve the efficiency of calculation.

Figure 3:
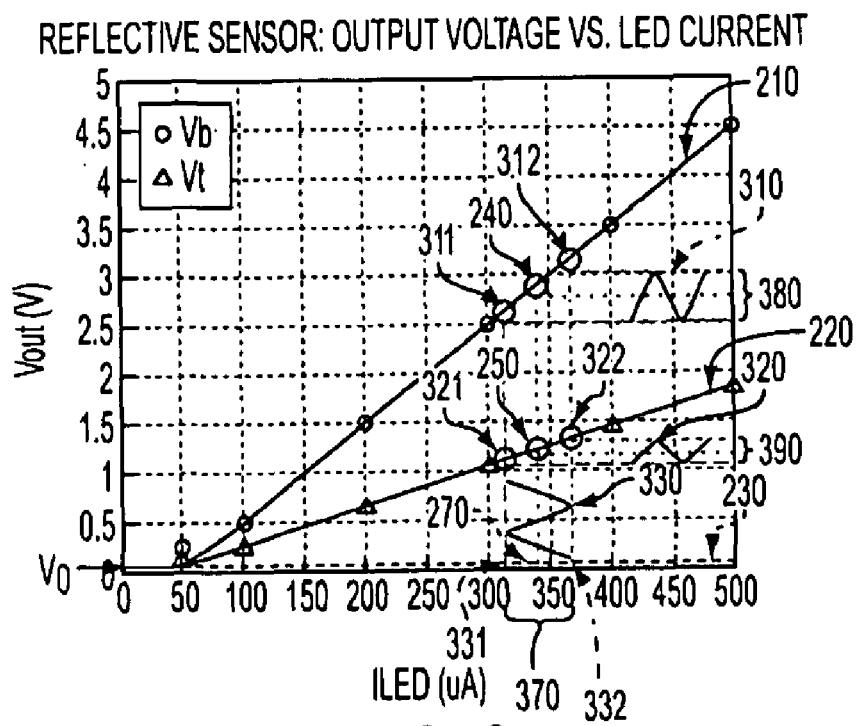
FIG. 3 is a diagram illustrating a modulated intensity method for detecting toner density based on the reflectance characteristic of an object.

FIG. 3 is a plot showing the same exemplary response characteristics of a sensor system as in FIG. 2. In addition, FIG. 3 can be used to illustrate various embodiments using emitted light of modulated intensity.

As shown in FIG. 3, the driving current of the emitter 110 can vary between 310 µA and 370 µA. Additionally, the driving current can vary according to different patterns. For example, the driving current can vary according to a step pattern. The driving current can keep at 310 µA for a certain time, then keep at 370 µA for a certain time. For another example, the driving current can vary according to a triangular pattern. The driving current can increase linearly from 310 µA to 370 µA, then the driving current can decrease linearly from 370 µA to 310 µA. For another specific example, the driving current can vary sinusoidally of a particular frequency, such as 330 shown in FIG. 3. The driving current can vary according to a single frequency sinusoidal pattern having a center current 340 µA, and an amplitude of 30 µA.

As discussed above, the emitter driving current can drive the emitter 110 to emit a light having an intensity that fluctuates with the emitter driving current. Thus, if the emitter driving current is modulated, the intensity of the emitted light from the emitter 110 can also be modulated. Accordingly, when the emitter driving current is sinusoidally modulated, the intensity of the emitted light can be sinusoidally modulated.

As already known, the light can be affected and reflected by the object 140. The reflected light can also be modulated when the emitted light is modulated. The reflected light can be detected by detector 120 and an intensity of the detected light can be converted into an output voltage signal. For a linear sensor system, the output voltage signal can vary linearly with respect to the variation of the emitted light. Therefore, when the emitted light is modulated, the output voltage of the detector 120 is modulated. Specifically, when the emitted light is sinusoidally modulated, the output voltage of the detector 120 can be sinusoidally modulated with the same frequency.

The linearity of the sensor system can be accomplished by carefully choosing sensor geometry, position of the light, optics for collecting the light, and electronics for post processing. The description below is based on the linearity of the sensor system.

As can be seen from FIG. 3, reflectance characteristics of a first portion and a second portion of the object 140 can be represented by the response characteristic lines 210 and 220, respectively. The first portion of the object 140 has a layer of the specific toner. The second portion of the object 140 is toner free. As can be inferred from FIG. 3, the specific toner can absorb light and reduce the intensity of the reflected light, so the output voltage of the first portion of the object 140 is generally smaller than second portion of the object 140, so the response characteristic line 220 has a smaller slope than toner free response characteristic line 210. Furthermore, larger toner density can result in even smaller slope for the response characteristic line 220.

As can be seen, when the emitter driving current changes, the intensity of the reflected light also changes. Because of the linearity of the sensor system, changes of the emitter driving current proportionally vary the intensity of reflected light from the object 140, which is subsequently detected by the detector 120. As a result, the output voltage of the detector 120 varies proportionally to changes of the emitter driving current. For example, when the emitter driving current varies between 310 μA and 370 μA, the difference 60 μA is a peak-to-peak amplitude of modulation of the emitter driving current. Accordingly, the output voltage corresponding to the first portion of the object 140 can vary between 1.05V and 1.3V. The difference 0.25V is a peak-to-peak amplitude of modulation. Similarly, the output voltage corresponding to the second portion of the object 140 can vary between 2.5V and 3V, and the difference 0.5V is a peak-to-peak amplitude of modulation of the output voltage. When the emitter driving current is sinusoidally modulated as indicated by 330, the output voltage corresponding to the first portion of the object 140 can be sinusoidally modulated as indicated by 320 and the output voltage corresponding to the second portion of the object 140 can be sinusoidally modulated as indicated by 310.

According to one embodiment, the amplitude of modulation of the output voltage can be used to evaluate the toner density. A modulation relationship with toner density can be pre-calibrated based on a constant status of the emitted light. The modulation relationship can relate amplitude of modulation to toner density. Therefore, an amplitude of modulation, such as the peak-to-peak amplitude of modulation 0.25V indicated by 390 in FIG. 3 can be related to a toner density.

The constant status of the emitted light can be maintained by occasionally calibrating the emitted light. For example, the amplitude of modulation of the driving current can be adjusted to ensure a reflected light from a surface of known property, such as a bare surface without toner, have constant amplitude of modulation. Alternatively, the emitted light can be split by a beam splitter. Then, the split light can be detected by another detector (not shown). The other detector can be coupled with the controller 130. Consequently, the controller 130 can adjust the emitter 110 to maintain the split light of constant amplitude of modulation, thus the emitted light can be kept at the constant status.

According to another embodiment, a ratio by dividing an amplitude of modulation of the reflected light by an amplitude of modulation of the emitted light can be used to evaluate the toner density. The amplitude of modulation of the emitted light can be the amplitude of modulation of the emitter driving current. Alternatively, the amplitude of modulation of the emitted light can be measured by a beam splitter with a detector as described above.

According to other embodiments, a relative reflectance of the object 140 can be calculated, such as the relative reflectance between a first portion of the object 140 and a second portion of the object 140. The first portion of the object 140 can have the layer of specific toner, and the second portion of the object 140 can be toner free. The relative reflectance can be used to evaluate the toner density of the specific toner at the first portion of the object 140.

The relative reflectance can be calculated by dividing a first ratio by a second ratio. The first ratio can be a ratio of two amplitudes corresponding to the first portion of the object 140. One is the amplitude of modulation of the detector output voltage corresponding to the first portion of the object, the other is the amplitude of modulation of the emitter driving current corresponding to the first portion of the object. Similarly, the second ratio can be a ratio of two amplitudes corresponding to the second portion of the object 140. One is the amplitude of modulation of the detector output voltage corresponding to the second portion of the object 140, the other is the amplitude of modulation of the emitter driving current corresponding to the second portion of the object 140. The calculation can be represented by equation 2:

$$RR = \frac{\frac{\text{Amplitude of Modulation } V_t}{\text{Amplitude of Modulation } I_{LED-t}}}{\frac{\text{Amplitude of Modulation } V_b}{\text{Amplitude of Modulation } I_{LED-b}}} \qquad (2)$$

where $I_{LED-t}$ is the emitter driving current corresponding to the first portion of the object 140. $I_{LED-b}$ is the emitter driving current corresponding to the second portion of the object 140. $V_t$ is the output voltage of the detector 120 in accordance to the first portion of the object 140. $V_b$ is the output voltage of the detector 120 in accordance to the second portion of the object 140.

When the amplitudes of modulation for the emitter driving current corresponding to the first and second portions of the object 140 are the same, the relative reflectance can be simplified as a ratio of two amplitudes of modulation of detector output voltage, one is corresponding the first portion of the object 140, the other is corresponding to the second portion of the object 140.

For example, as shown in FIG. 3, the peak-to-peak amplitude of modulation of the emitter driving current is 60 μA for both the first and second portions of the object 140. The amplitude of modulation of the output voltage corresponding to the first portion is 0.25V, and the amplitude of the output voltage corresponding to the second portion is 0.5V. Therefore, the first ratio is 0.25/60(V/μA), and the second ratio is 0.5/60(V/μA). Thus, the relative reflectance can be calculated by dividing the first ratio by the second ratio, and the result is 0.5.

According to the same example, since the amplitudes of modulation of the emitter driving current are the same, the relative reflectance can be calculated by dividing the amplitude of modulation of the output voltage corresponding to the first portion, which is 0.25V, by the amplitude of modulation of the output voltage corresponding to the second portion, which is 0.5V, the result is also 0.5.

According to another embodiment, the amplitude of modulation can be calculated more robustly and efficiently by analog filtering or signal processing techniques, such as Fourier transform and digital filtering. For example, when the emitter driving current is sinusoidally modulated with a specific frequency, the output voltage of the detector 130 can have a corresponding component that is also sinusoidally modulated with the specific frequency. The output voltage of the detector 130 can have other components that are corresponding to the noises. The noise components can have different frequencies from the specific frequency. While the specific frequency is known, the amplitude of modulation of the output voltage, which is corresponding to the modulated emitter driving current, can be extracted by standard signal processing techniques, such as Fourier transform. Consequently, the noises can be excluded from further calculation. Thus, a more accurate detection of the relative reflectance can be achieved.

Figure 4:
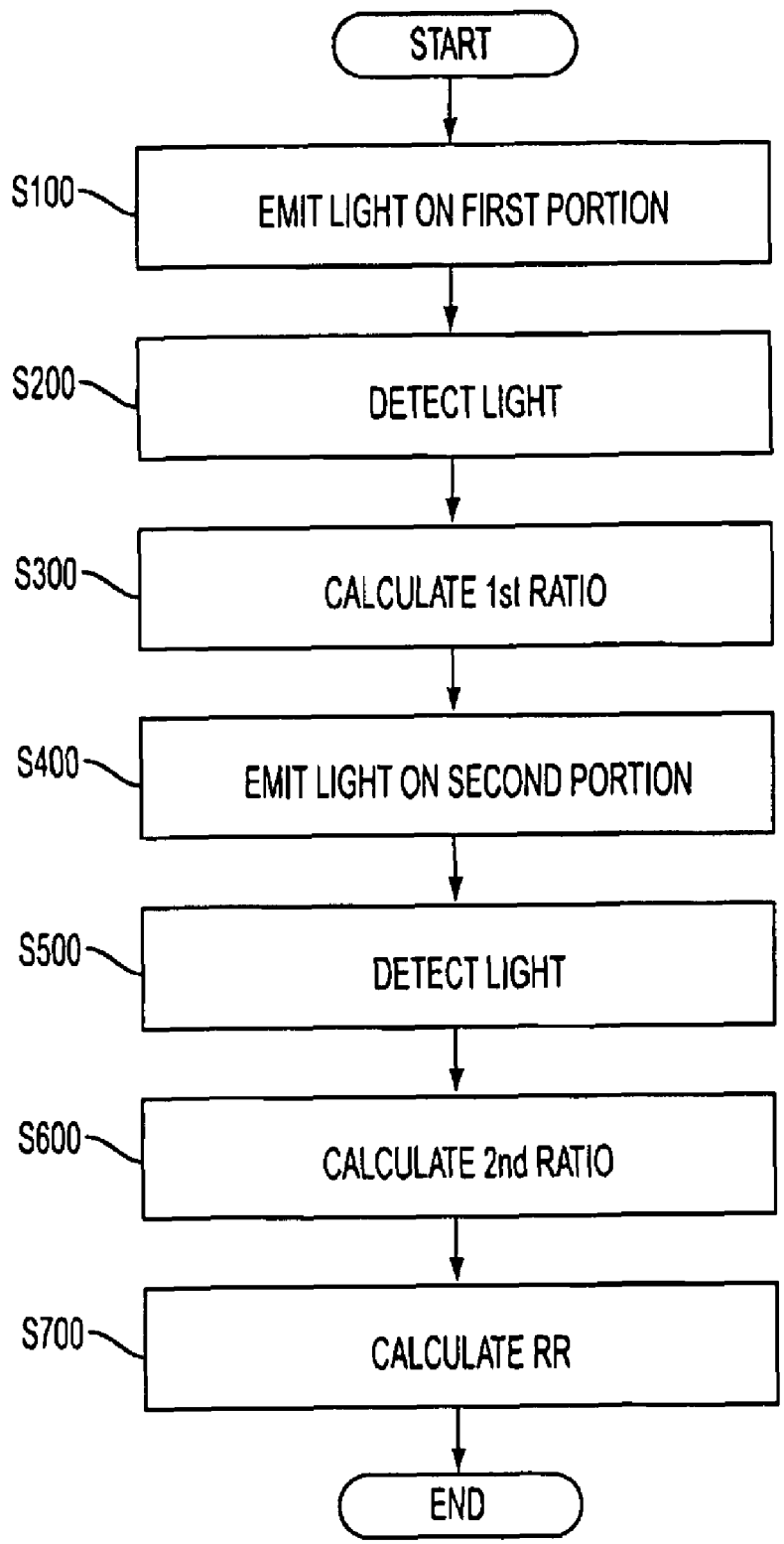
FIG. 4 is a flowchart illustrating an exemplary process of modulating light intensity for detecting a relative reflectance of an object.

FIG. 4 is a flowchart outlining an exemplary procedure for detecting the relative reflectance by using light of modulated intensity. The method begins in step S100, wherein a first light of modulated intensity is emitted to a first portion of an object. The process then proceeds to step S200, wherein a first reflected light is detected.

The process proceeds to step S300, wherein a first ratio is calculated by dividing an amplitude of the first reflected light by an amplitude of the first emitted light. The process proceeds to step S400, wherein a second light of modulated intensity is emitted to the second portion of the object. The process proceeds to step S500, wherein a second reflected light is detected.

The process proceeds to step S600, wherein a second ratio is calculated by dividing an amplitude of the second reflected light by an amplitude of the second emitted light. The process then proceeds to step S700, wherein the relative reflectance is calculated by dividing the first ratio by the second ratio. Then the process ends.

The disclosure can use different ranges of driving current for the portion of the object with or without toner, which can decouple the reflectance detection of the two circumstances.

The disclosure does not need a complex test pattern, and the extraction of amplitude of the modulated signal can be performed by the standard signal processing techniques, which can be done quickly and easily.

Additionally, modulating LED intensity can reduce the duty cycle of the incident light, which can minimize the effect of light shock or other unintentional discharge of the charged surfaces, such as photoreceptor surface.

For the ease of description, the disclosure is presented with reference to measuring parameters of photoreceptor surface. However, the disclosure can be used on measuring parameters of various surfaces, such as intermediate transfer belt, paper or other substrates.

For the ease of description, the disclosure is presented with reference to measure parameters of toners in a xerographic printer. However, the disclosure can be used on measuring parameters of various printers, such as water based inkjet or wax-based inkjet. In addition, the disclosure can be used on measuring parameters of various pigments or various dyes, such as ink, or toner.

For the ease of description, the disclosure is presented with reference to relative reflectance of an optical densitometer. However, the disclosure can be used on various sensor systems as long as the linearity can be assumed in the operating range. The disclosure can also be used for detecting other optical properties, such as transmissive property.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A method of detecting a density of a pigmented layer on an object, comprising:
   emitting a first modulated light onto a first portion of the object having the pigmented layer;
   detecting a first reflected light of the first modulated light from the first portion of the object; and
   determining the density of the pigmented layer according to the first reflected light, wherein determining the density of the pigmented layer includes:
   emitting a second modulated light onto a second portion of the object;
   detecting a second reflected light of the second modulated light from the second portion of the object; and
   determining the density of the pigmented layer according to a relative ratio that is related to the first reflected light and the second reflected light.

2. The method of detecting the density of the pigmented layer on the object according to claim 1, wherein determining the density of the pigmented layer according to the first reflected light, further comprises:
   keeping a constant status of the first modulated light;
   pre-calibrating a density relationship with the reflected light based on the constant status of the first modulated light; and
   determining the density of the pigmented layer according to the first reflected light and the density relationship with the reflected light.

3. The method of detecting the density of the pigmented layer on the object according to claim 2, wherein keeping the constant status of the first modulated light, further comprises:
   calibrating the constant status according to a known density.

4. The method of detecting the density of the pigmented layer on the object according to claim 2, wherein keeping the constant status of the first modulated light, further comprises:
   monitoring the status of the first modulated light; and
   controlling the status of the first modulated light according to a feedback of the monitored status of the first modulated light.

5. The method of detecting the density of the pigmented layer on the object according to claim 1, wherein determining the density of the pigmented layer according to the first reflected light, further comprises:
   calculating a ratio of an amplitude of the first reflected light by an amplitude of the first modulated light; and
   determining the density of the pigmented layer according to the ratio.

6. The method of detecting the density of the pigmented layer on the object according to claim 5, wherein the amplitude of the first modulated light is measured through a beam splitter and a detector.

7. The method of detecting the density of the pigmented layer on the object according to claim 5, wherein the amplitude of the first modulated light is calculated using an amplitude of a first driving current.

8. The method of detecting the density of the pigmented layer on the object according to claim 5, wherein the amplitude of the first reflected light is detected by at least one of analog filtering, signal processing techniques including Fourier analysis, and digital filtering.

9. The method of detecting the density of the pigmented layer on the object according to claim 1, wherein the first modulated light is modulated periodically with a first frequency.

10. The method of detecting the density of the pigmented layer on the object according to claim 1, wherein determining the density of the pigmented layer according to the relative ratio that is related to the first reflected light and the second reflected light, further comprises:
calculating the relative ratio by dividing an amplitude of the first reflected light by an amplitude of the second reflected light.

11. The method of detecting the density of the pigmented layer on the object according to claim 10, wherein the amplitude of the first reflected light is detected by at least one of analog filtering, signal processing techniques including Fourier analysis, and digital filtering.

12. The method of detecting the density of the pigmented layer on the object according to claim 10, wherein the amplitude of the second reflected light is detected by at least one of analog filtering and signal processing techniques including Fourier analysis, and digital filtering.

13. The method of detecting the density of the pigmented layer on the object according to claim 1, wherein determining the density of the pigmented layer according to the relative ratio that is related to the first reflected light and the second reflected light, further comprises:
calculating a first ratio by dividing an amplitude of the first reflected light by an amplitude of the first modulated light;
calculating a second ratio by dividing an amplitude of the second reflected light by an amplitude of the second modulated light; and
calculating the relative ratio by dividing the first ratio by the second ratio.

14. The method of detecting the density of the pigmented layer on the object according to claim 13, wherein the amplitude of the first modulated light is measured through a beam splitter and a detector.

15. The method of detecting the density of the pigmented layer on the object according to claim 13, wherein the amplitude of the first modulated light is calculated using an amplitude of a first modulated driving current.

16. The method of detecting the density of the pigmented layer on the object according to claim 13, wherein the amplitude of the second modulated light is measured through a beam splitter and a detector.

17. The method of detecting the density of the pigmented layer on the object according to claim 13, wherein the amplitude of the second modulated light is calculated using an amplitude of a second modulated driving current.

18. The method of detecting the density of the pigmented layer on the object according to claim 13, wherein the first modulated light is modulated by at least one of sinusoidal, triangular, and step patterns.

19. The method of detecting the density of the pigmented layer on the object according to claim 13, wherein the second modulated light is modulated by at least one of sinusoidal, triangular, and step patterns.

20. The method of detecting the density of the pigmented layer on the object according to claim 13, wherein the amplitude of the first reflected light is detected by at least one of analog filtering, signal processing techniques including Fourier analysis, and digital filtering.

21. The method of detecting the density of the pigmented layer on the object according to claim 13, wherein the amplitude of the second reflected light is detected by at least one of analog filtering and signal processing techniques including Fourier analysis, and digital filtering.

22. The method of detecting the density of the pigmented layer on the object according to claim 13, wherein the first modulated light is modulated periodically with a first frequency.

23. The method of detecting the density of the pigmented layer on the object according to claim 13, wherein the second modulated light is modulated periodically with a second frequency.

24. A sensor system that detects a density of a pigmented layer of an object, comprising:
an emitter that emits a modulated light onto a portion of the object, the object including a first portion that has a pigmented layer and a second portion that is bare, wherein the emitter emits a first modulated light onto the first portion of the object and emits a second modulated light onto the second portion of the object;
a detector that detects a reflected light from the portion of the object, the detected reflected light including a first reflected light from the first portion of the object and a second reflected light from the second portion of the object; and
a controller that is coupled to the emitter and the detector, the controller determines the density of the pigmented layer of the object based on the detected first reflected light and the detected second reflected light, wherein the density of the pigmented layer is determined according to a relative ratio that is related to the first reflected light and the second reflected light.

25. The sensor system that detects the density of the pigmented layer of the object according to claim 24, further comprises:
a memory unit that stores a pre-calibrated density relationship with reflected light based on a constant status of the modulated light, the controller determines the density of the pigmented layer according to the density relationship with reflected light and the detected reflected light.

26. The sensor system that detects the density of the pigmented layer of the object according to claim 25, wherein the constant status of the modulated light is kept by calibrating the constant status according to a known density.

27. The sensor system that detects the density of the pigmented layer of the object according to claim 25, further comprises:
a beam splitter that splits a portion of the modulated light; and
a split beam detector that detects the split portion of modulated light.

28. The sensor system that detects the density of the pigmented layer of the object according to claim 27, the controller controls the modulated light at the constant status by controlling the split portion of the modulated light.

29. The sensor system that detects the density of the pigmented layer of the object according to claim 24, wherein the controller determines the density of the pigmented layer by:
    calculating a ratio of an amplitude of the reflected light by an amplitude of the modulated light; and
    determining the density of the pigmented layer according to the ratio.

30. The sensor system that detects the density of the pigmented layer of the object according to claim 29, wherein the amplitude of the modulated light is calculated using an amplitude of a driving current.

31. The sensor system that detects the density of the pigmented layer of the object according to claim 29, wherein the modulated light is modulated periodically.

32. The sensor system that detects the density of the pigmented layer of the object according to claim 24, wherein the controller calculates the relative ratio by dividing an amplitude of the first reflected light by an amplitude of the second reflected light.

33. The sensor system that detects the density of the pigmented layer of the object according to claim 24, wherein the controller
    calculates a first ratio by dividing an amplitude of the first reflected light by an amplitude of the first modulated light;
    calculates a second ratio by dividing an amplitude of the second reflected light by an amplitude of the second modulated light; and
    calculates the relative ratio by dividing the first ratio by the second ratio.

34. A printing system, comprising:
an object that is at least one of a photoreceptor drum, a photoreceptor belt, an intermediate transfer belt, an intermediate transfer drum and paper, the object including a first portion that has a pigmented layer and a second portion that is bare;
a sensor system that detects a density of the pigmented layer of the object, comprising:
    an emitter that emits a modulated light onto a portion of the object, wherein the emitter emits a first modulated light onto the first portion of the object and a second modulated light onto the second portion of the object;
    a detector that detects a first reflected light from the first portion of the object and a second reflected light from the second portion of the object; and
    a controller that is coupled to the emitter and the detector, the controller determines the density of the pigmented layer of the object based on the reflected light and adjusts the printing system according to the density of the pigmented layer, wherein the density of the pigmented layer is determined according to a relative ratio that is related to the first reflected light and the second reflected light.

* * * * *